US010168428B2

(12) United States Patent
Savord

(10) Patent No.: US 10,168,428 B2
(45) Date of Patent: Jan. 1, 2019

(54) ULTRASOUND TRANSDUCER ARRAYS WITH VARIABLE PATCH GEOMETRIES

(71) Applicant: KONINKLIJKE PHILIPS N.V., Eindhoven (NL)

(72) Inventor: Bernard Joseph Savord, Andover, MA (US)

(73) Assignee: Koninklijke Philips N.V., Eindhoven (NL)

(*) Notice: Subject to any disclaimer, the term of this patent is extended or adjusted under 35 U.S.C. 154(b) by 21 days.

(21) Appl. No.: 15/616,998

(22) Filed: Jun. 8, 2017

(65) Prior Publication Data

US 2017/0269208 A1    Sep. 21, 2017

Related U.S. Application Data

(63) Continuation of application No. 14/397,494, filed as application No. PCT/IB2013/053328 on Apr. 26, 2013, now Pat. No. 9,739,885.

(60) Provisional application No. 61/644,524, filed on May 9, 2012.

(51) Int. Cl.
*G01S 15/89* (2006.01)
*G01S 7/52* (2006.01)
*A61B 8/00* (2006.01)
*G10K 11/34* (2006.01)

(52) U.S. Cl.
CPC ........ *G01S 15/8925* (2013.01); *A61B 8/4488* (2013.01); *G01S 7/5208* (2013.01); *G01S 7/52095* (2013.01); *G01S 15/8927* (2013.01); *G01S 15/8993* (2013.01); *G10K 11/346* (2013.01)

(58) Field of Classification Search
CPC ............. G01S 15/8925; G01S 7/52095; G01S 7/5208; A61B 8/4488
See application file for complete search history.

(56) References Cited

U.S. PATENT DOCUMENTS

| 4,797,682 A | 1/1989 | Klimczak |
| 5,229,933 A | 7/1993 | Larson |
| 5,431,167 A | 7/1995 | Savord |
| 5,677,491 A | 10/1997 | Ishrak et al. |
| 5,832,923 A | 11/1998 | Engeler et al. |

(Continued)

FOREIGN PATENT DOCUMENTS

| CN | 101416070 A | 4/2009 |
| EP | 1491913 A2 | 12/2004 |

OTHER PUBLICATIONS

Tao et al "Simulation of Focusing Performance of Annular Ultrasonic Transducer With Varying Aperture" Technical Acoustics, vol. 26, No. 2, Apr. 2007 (English Abstract and CN Article).

*Primary Examiner* — Hovhannes Baghdasaryan

(57) ABSTRACT

A two dimensional ultrasonic array transducer receives echo signals from increasing depths of a volumetric region. The 2D array is configured into patches of elements which are processed by a microbeamformer and summed signals from a patch are coupled to a channel of an ultrasound beamformer At the shallowest depth the 2D array receives echoes from small patches in the center of the aperture. As signals are received from increasing depths the aperture is grown by symmetrically adding patches of progressively larger sizes on either side of the small patches in the center. The inventive technique can improve the multiline performance of both 1D and 2D array probes.

15 Claims, 8 Drawing Sheets

(56) References Cited

U.S. PATENT DOCUMENTS

| | | |
|---|---|---|
| 5,911,221 A | 6/1999 | Teo |
| 7,927,280 B2 | 4/2011 | Davidsen |
| 2001/0051772 A1 | 12/2001 | Bae |
| 2003/0045794 A1 | 3/2003 | Bae |
| 2003/0216645 A1 | 11/2003 | Yao |
| 2005/0033170 A1 | 2/2005 | Angelsen et al. |
| 2005/0131299 A1 | 6/2005 | Robinson et al. |
| 2005/0243812 A1 | 11/2005 | Phelps |
| 2008/0021324 A1 | 1/2008 | Seto |
| 2008/0106976 A1 | 5/2008 | Davidsen et al. |
| 2009/0005684 A1 | 1/2009 | Kristoffersen et al. |
| 2009/0069692 A1 | 3/2009 | Cooley et al. |
| 2009/0171213 A1 | 7/2009 | Savord |
| 2011/0319764 A1 | 12/2011 | Okada et al. |
| 2012/0143100 A1 | 6/2012 | Jeong et al. |
| 2012/0323121 A1 | 12/2012 | Miller |
| 2014/0121531 A1 | 5/2014 | Poland |

ULTRASOUND TRANSDUCER ARRAYS WITH VARIABLE PATCH GEOMETRIES

The present application is a continuation of U.S. patent application Ser. No. 14/397,494 filed Oct. 28, 2014, which is the U.S. National Phase application under 35 U.S.C. §371 of International Application No. PCT/IB2013/053328, filed Apr. 26, 2013, which claims the benefit of U.S. Provisional Application Ser. No. 61/644,524 filed May 9, 2012. These applications are hereby incorporated by reference herein.

This invention relates to medical diagnostic ultrasound systems and, in particular, to diagnostic systems with array transducers having elements grouped in patches and operating with a microbeamformer.

Ultrasound array transducers, transducers with a plurality of separately controllable transducer elements, have been developed in a number of configurations. Annular arrays are comprised of annular rings of elements and are well suited to transmit a tightly focused beam straight ahead, that is, normal to the plane of the transducer elements. A 1D array of elements is comprised of a single row of elements (or multiple rows connected to operate in unison) which can scan a single image plane, an azimuth plane, normal to the row of elements. A 1.5D array comprises multiple rows of elements which can be operated symmetrically in elevation to scan an azimuth plane normal to the array but with beams that are focused electronically in both azimuth and elevation. A 2D (two dimensional) array comprises elements extending in both azimuth and elevation directions which can be operated fully independently to both focus and steer beams in any azimuth or elevation direction. Except for the annular array, these arrays can be configured in either flat or curved orientations. The present invention is directed to 2D array transducers which can steer and focus in both azimuth and elevation to scan a three dimensional volumetric region of interest.

Two dimensional array transducers and even 1D array with large numbers of elements pose a problem due to their large number of transducer elements. Since each of these elements must be individually controlled on transmit and receive, a separate signal line must be provided for each element. A 1D array may comprise a row of 100-200 elements, requiring 100-200 signal lines, which can be accommodated in a relatively small and light probe cable, but may need to operate with a system beamformer of relatively few channels. A 2D array may have 100-200 rows of elements in one dimension and 100-200 columns of elements in the other dimension, totaling thousands of individual elements. A cable of many thousands of signal lines is not practical for a probe which hand-held and must be manipulated by the sonographer. An implementation of the present invention overcomes these problems by use of a microbeamformer integrated circuit attached to the 2D array which performs partial beamforming of groups of elements referred to as patches. The summed signal from the elements of each patch are then conducted over a standard size cable to the ultrasound system beamformer where the summed signal from each patch is applied to a channel of the system beamformer, which completes the beamforming operation. This partitioning of the full beamforming operation between a microbeamformer in the probe and the channels of the system beamformer, illustrated for instance in U.S. Pat. No. 5,229,933 (Larson, III), enable the use of a cable with a relatively few number of signal lines between the probe and the ultrasound system.

The number of elements used to receive echo signals from along a scanline can be selected and varied, thereby controlling the active aperture of the array. Much like an optical system, the number of elements in the active aperture relate to the f number of the aperture. As echoes are received from the near field immediately in front of the array, only a small number of elements can be used to receive the initial echo signals from a shallow depth of the beam. But as echoes are received from ever increasing depths, additional elements on either side of the initially used elements can be added in uniform increments to maintain the f number of the aperture and the sensitivity of the probe to echoes from greater depths. This dynamic aperture control is well understood for 1D arrays but becomes much more complex when a 2D array is used or multiline reception is needed. In multiline reception, echo signals received from transducer elements for multiple, spatially discrete lines are processed differently for the different lines and multiple receive lines are produced at the same time. See, for example, U.S. Pat. No. 5,431,167 (Savord). A microbeamformer with multiple parallel processors for each transducer element of a 2D array would be exceedingly complex, expensive, and constrained by the space available in the handheld transducer probe. But multiline reception is highly desirable for many probes, particularly for a 2D array due to need to transmit and receive beams over a volumetric region within the time limit of an acceptable acquisition frame rate and the speed of sound is an immutable law of physics. Hence a technique is needed to be able to perform high order multiline reception while maintaining high quality, artifact-free performance.

In accordance with the principles of the present invention, an ultrasonic transducer array is operated with a microbeamformer to process signals from defined patches of transducer elements. During reception from the near field a first patch size is used, preferably the smallest patch size in most implementations. As echoes are received from increasing depths of field the aperture grows by adding patches of different and preferably progressively larger size to the active aperture as the patch acceptance angle for echoes from greater depths declines. An implementation of the present invention enables the reception of a high order of multilines without artifacts and image brightness discontinuities.

Figure 1:
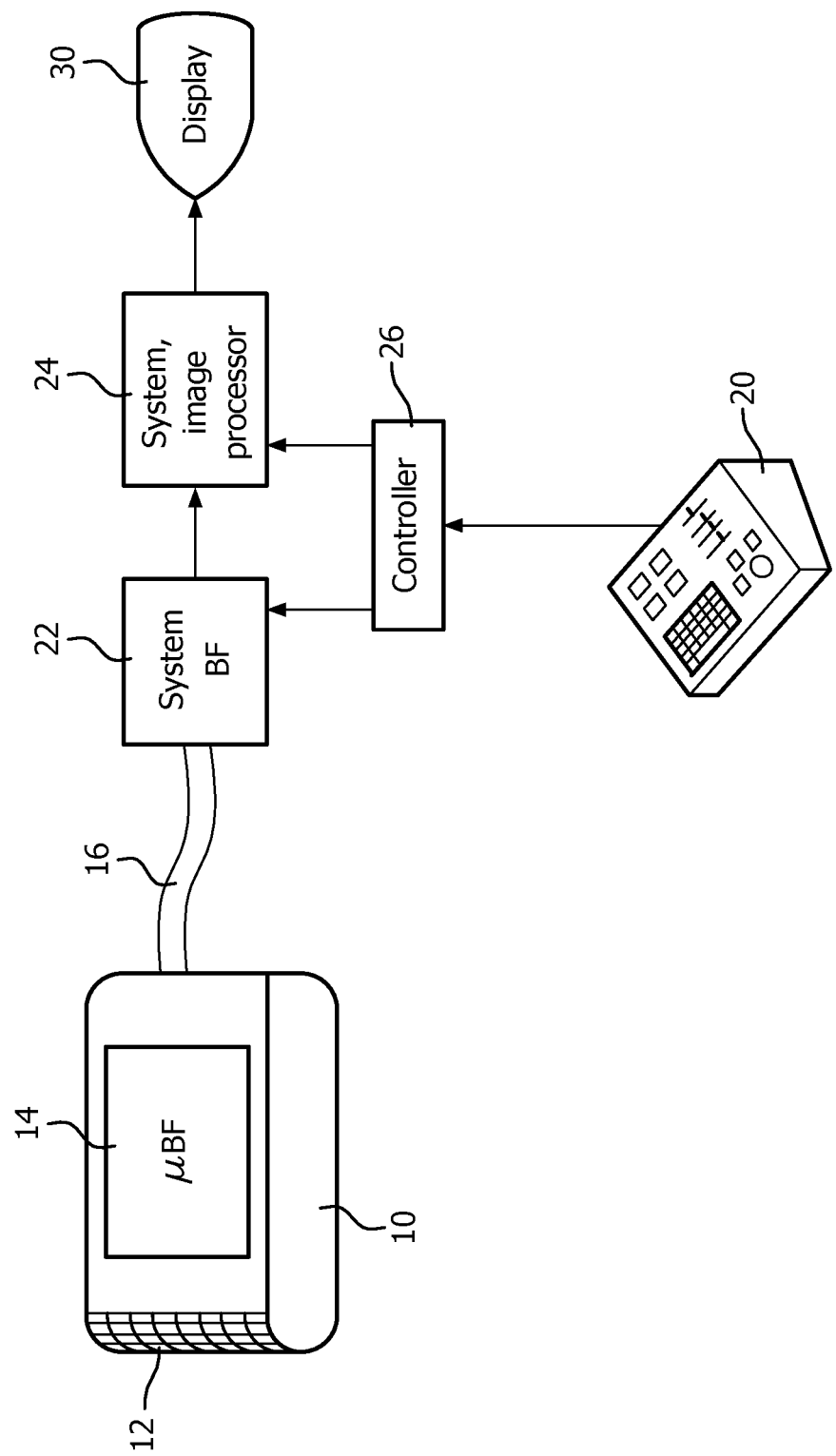
FIG. 1 illustrates in block diagram form a 2D curved array transducer and microbeamformer probe of the present invention.

Referring first to FIG. 1, an ultrasound system constructed in accordance with the principles of the present invention is shown in block diagram form. A probe 10 has a two dimensional array transducer 12 which is curved in the elevation dimension such as that shown in U.S. Pat. No. 7,927,280 (Davidsen). The elements of the array are coupled to a microbeamformer 14 located in the probe behind the transducer array. The microbeamformer applies timed transmit pulses to elements of the array to transmit beams in the desired directions and to the desired focal points in the three dimensional image field in front of the array. Echoes from the transmitted beams are received by the array elements and coupled to channels of the microbeamformer 14 where they are individually delayed. The delayed signals from a patch of transducer elements are combined to form a partial sum signal for the patch. As used herein the term "patch" refers to a group of transducer elements which are contiguous and operated together, or have their signals combined by a microbeamformer to form one signal for an ultrasound system beamformer. In a typical implementation combining is done by coupling the delayed signals from the elements of the patch to a common bus, obviating the need for summing circuits or other complex circuitry. The bus of each patch is coupled to a conductor of a cable 16, which conducts the partial sum patch signal to the system mainframe. In the system mainframe the partial sum signals are digitized and coupled to channels of a system beamformer 22, which appropriately delays each partial sum signal. The delayed partial sum signals are then combined to form a coherent steered and focused receive beam. The beam signals from the 3D image field are processed by a signal and image processor 24 to produce 2D or 3D images for display on an image display 30. Control of ultrasound system parameters such as probe selection, beam steering and focusing, and signal and image processing is done under control of a controller 26 which is coupled to various modules of the system. In the case of the probe 10 some of this control information is provided from the system mainframe over data lines of the cable 16. The user controls these operating parameters by means of a control panel 20.

Figure 2:
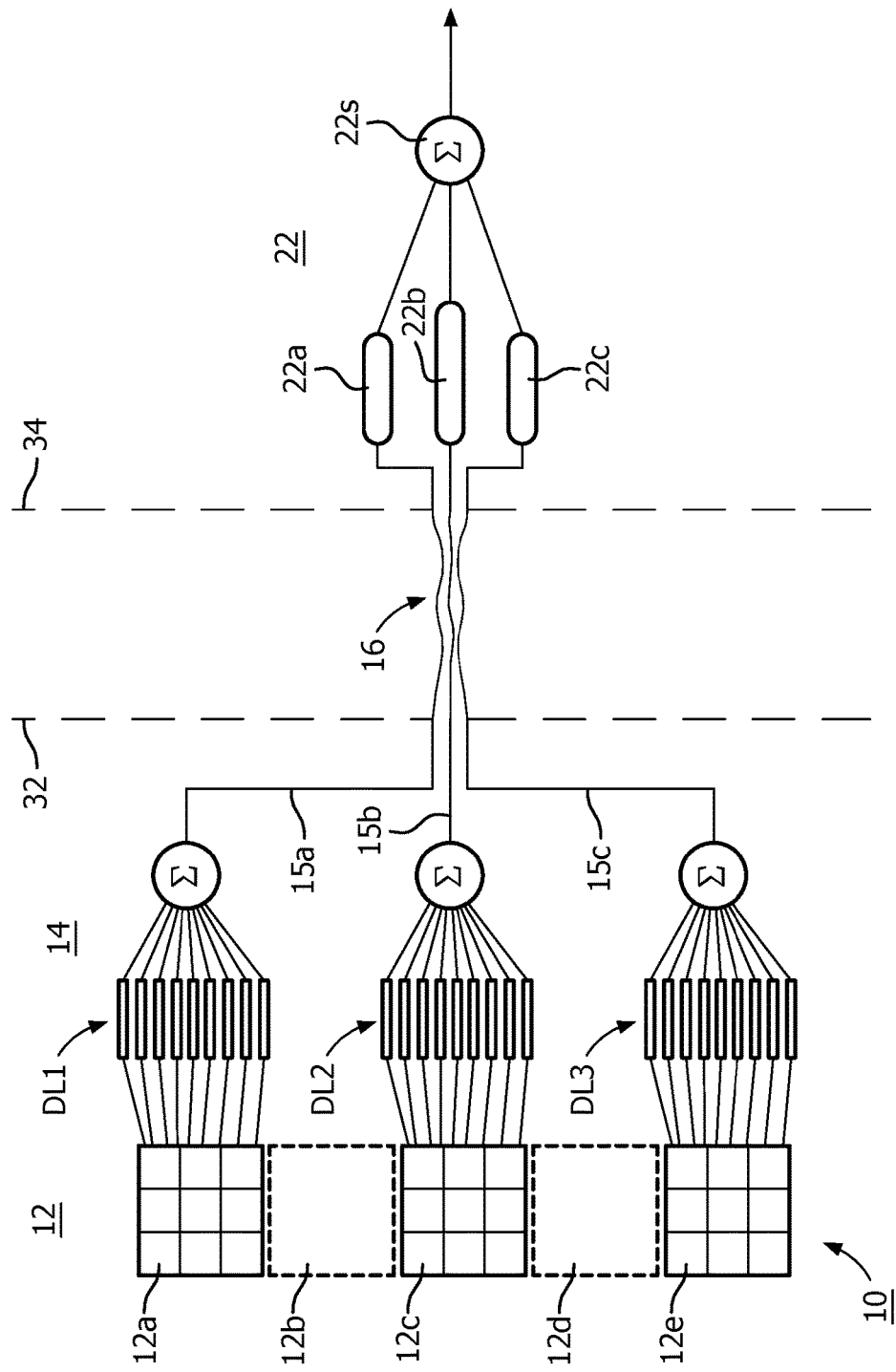
FIG. 2 is a block diagram illustrating the concept of a partial beamsum microbeamformer.

FIG. 2 illustrates the concept of a partially summing microbeamformer. The drawing of FIG. 2 is sectioned into three areas by dashed lines 32 and 34. Components of the probe 10 are shown to the left of line 32, components of the system mainframe are shown to the right of line 34, and the cable 16 is shown between the two lines. The two dimensional array 12 of the probe is divided into patches of contiguous transducer elements. Five of the patches of the array 12 are shown in the drawing, each including nine neighboring elements. The microbeamformer channels for patches 12a, 12c, and 12e are shown in the drawing. The nine elements of patch 12a are coupled to nine delay lines of the microbeamformer indicated at DL1. Similarly the nine elements of patches 12c and 12e are coupled to the delay lines indicated at DL2 and DL3. The delays imparted by these delay lines are a function of numerous variables such as the size of the array, the element pitch, the spacing and dimensions of the patch, the range of beam steering, and others. The delay line groups DL1, DL2, and DL3 each delay the signals from the elements of their respective patch to a common time reference for the patch. The nine delayed signals from each group of delay lines are then combined by a respective summer Σ to form a partial sum signal of the array from the patch of elements. Each partial sum signal is put on a separate bus 15a, 15b, and 15c, each of which is coupled to a conductor of the cable 16, which conducts the partial sum signals to the system mainframe. In the system mainframe each partial sum signal is applied to a delay line 22a, 22b, 22c of the system beamformer 22. These delay lines focus the partial sum signals into a common beam at the output of the system beamformer summer 22s. The fully formed beam is then forwarded to the signal and image processor for further processing and display. While the example of FIG. 2 is shown with 9-element patches, it will be appreciated that a constructed microbeamformer system will generally have patches with larger numbers of elements such as 12, 20, 48, or 70 elements or more. The elements of a patch can be adjacent to each other, be spaced apart, or even intermingled in a checkerboard pattern, with "odd" numbered elements combined in one patch and "even" numbered elements combined in another. The patches can be square, rectangular, diamond-shaped, hexagonal, or any other desired shape.

Figure 3A:
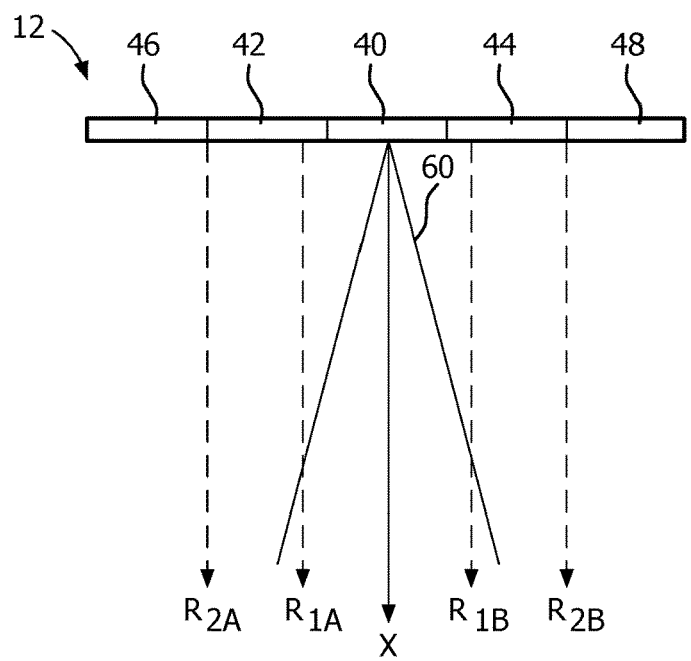
FIG. 3a illustrates multiline reception with a 2D array transducer using uniform patch sizes.

FIG. 3a illustrates a problem with multiline acquisition that can be addressed with an implementation of the present invention. FIG. 3a illustrates a receive beam profile 60, the outline of the area or volume of an image field in which echoes are received down to a depth X in the field. Four multilines $R_{1A}$, $R_{2A}$, $R_{1B}$, and $R_{2B}$, are to be received on either side of the line at the center of the image field by an array transducer 12 which is operationally divided into five patches of equal size, 40, 42, 44, 46 and 48. As is illustrated by FIG. 3a, the beam profile 60 of a set of uniformly sized patches 40-48 is a relatively narrow region in the center of the image field. Only the deepest depths of the two multilines closest to the field center, $R_{1A}$ and $R_{1B}$, are within the receive beam profile. The rest of the extent of the $R_{1A}$ and $R_{1B}$ multilines and the full extent of the outer multilines $R_{2A}$ and $R_{2B}$ are beyond the receive beam profile. Consequently the received signals for these beams will be of low intensity, resulting in weakly received echo signals which will be only dimly shown in an image using these multilines. The resulting artifacts will appear as shimmering bands of light and dark streaks in the resultant ultrasound image.

Figure 3B:
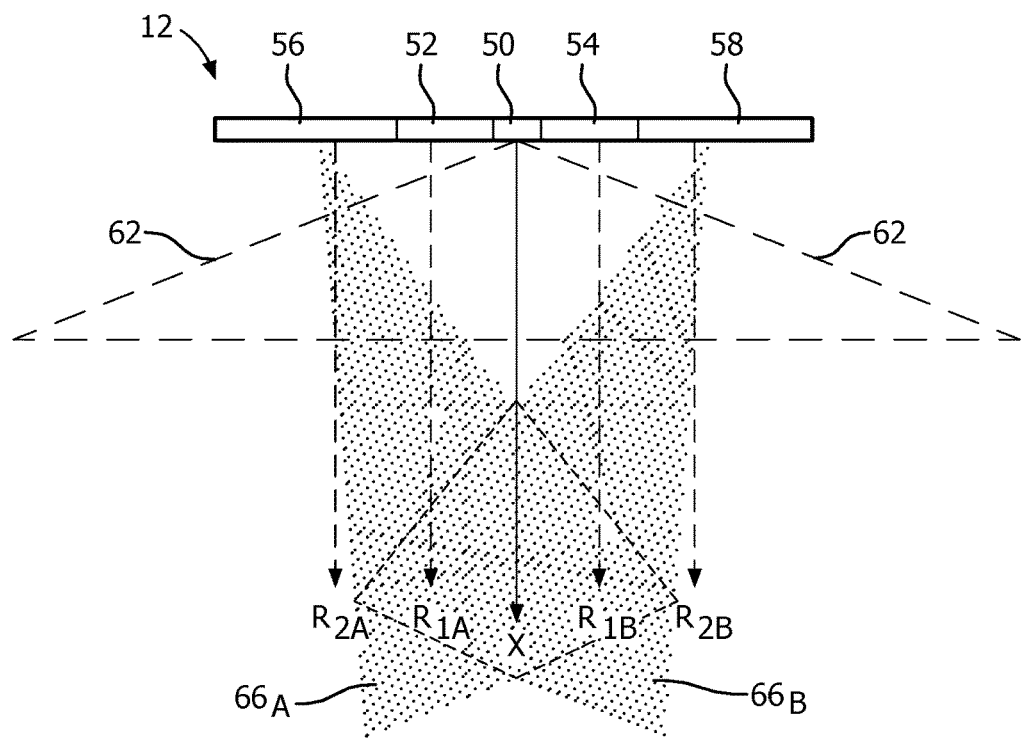
FIG. 3b illustrates multiline reception with a 2D array transducer using progressively larger patch sizes in accordance with the principles of the present invention.
Figure 3C:
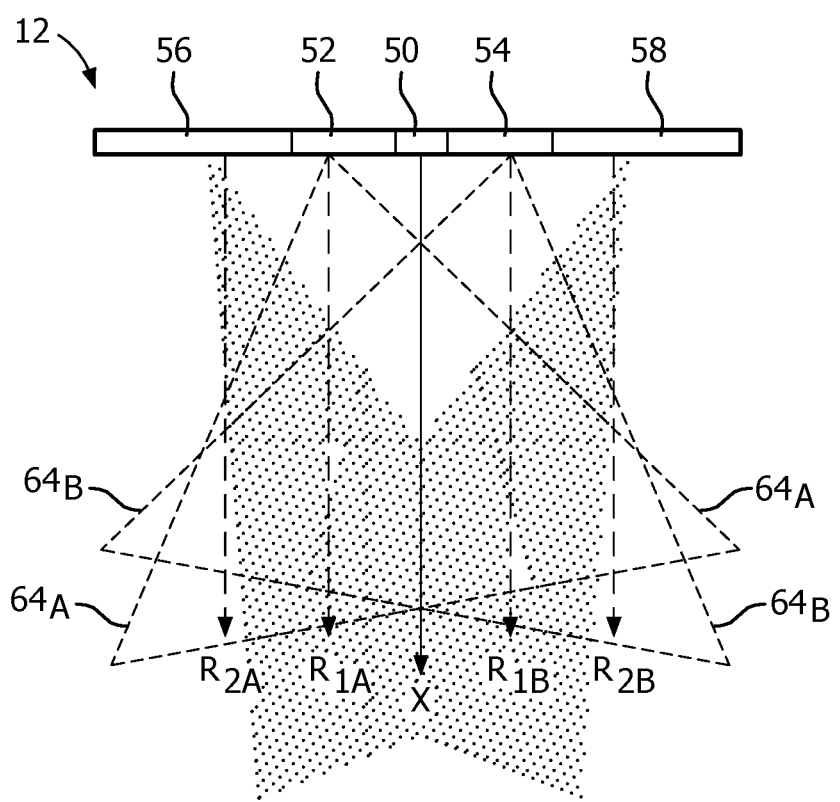
FIG. 3c is another illustration of the drawing of FIG. 3b which highlights the beam profiles of the intermediate-sized patches.

In FIG. 3b, patches of different sizes are progressively added to the aperture to provide full coverage of the received echoes for the multilines. The center patch 50 is the smallest, which gives it the greatest acceptance angle for received echoes and a receive beam profile 62 which is relatively shallow in depth yet laterally broad as shown in FIG. 3b. The receive beam profile 62 for this small center patch is seen to cover the near field of all four multilines. The adjacent patches 52 and 54 on either side of the center patch 50 are added as echoes are received from greater depths and cover the reception of mid-depth echoes of all four multilines as shown in FIG. 3c. The beam profiles 64A and 64B obtained with the addition of the two larger patches 52 and 54 are seen to span all four multilines. The beam profiles from each of the larger patches are also seen to be slightly steered toward the center of the image field to provide complete coverage of the scanned region. Finally, the outermost, even larger patches 56 and 58 are added to the active aperture. The receive beam profiles $66_A$ and $66_B$ obtained with these patches are shown in FIG. 3b. These beam profiles extend to the greatest depths of the image field, are seen to have the smallest acceptance angles of any of the beam profiles, and are also seen to be slightly steered toward the center of the image field to afford full coverage of the region being scanned. The combination of all of the patches of the different sizes afford full coverage of the image field, preventing reception of echoes from outside of a beam profile and resulting shimmering image artifacts.

Figure 4:
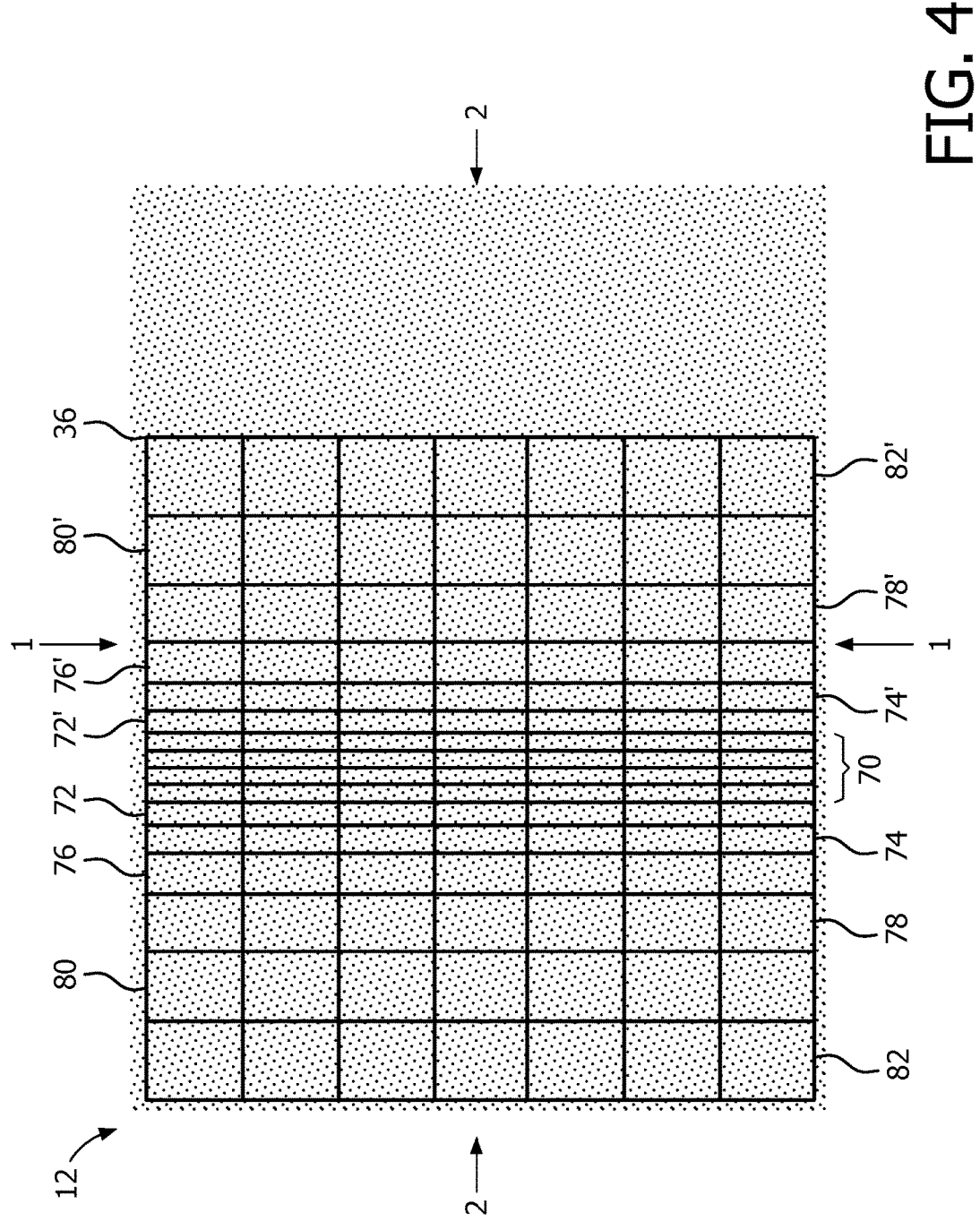
FIG. 4 illustrates the patch areas for azimuth scanning with a 2D array transducer constructed in accordance with the principles of the present invention.
Figure 5:
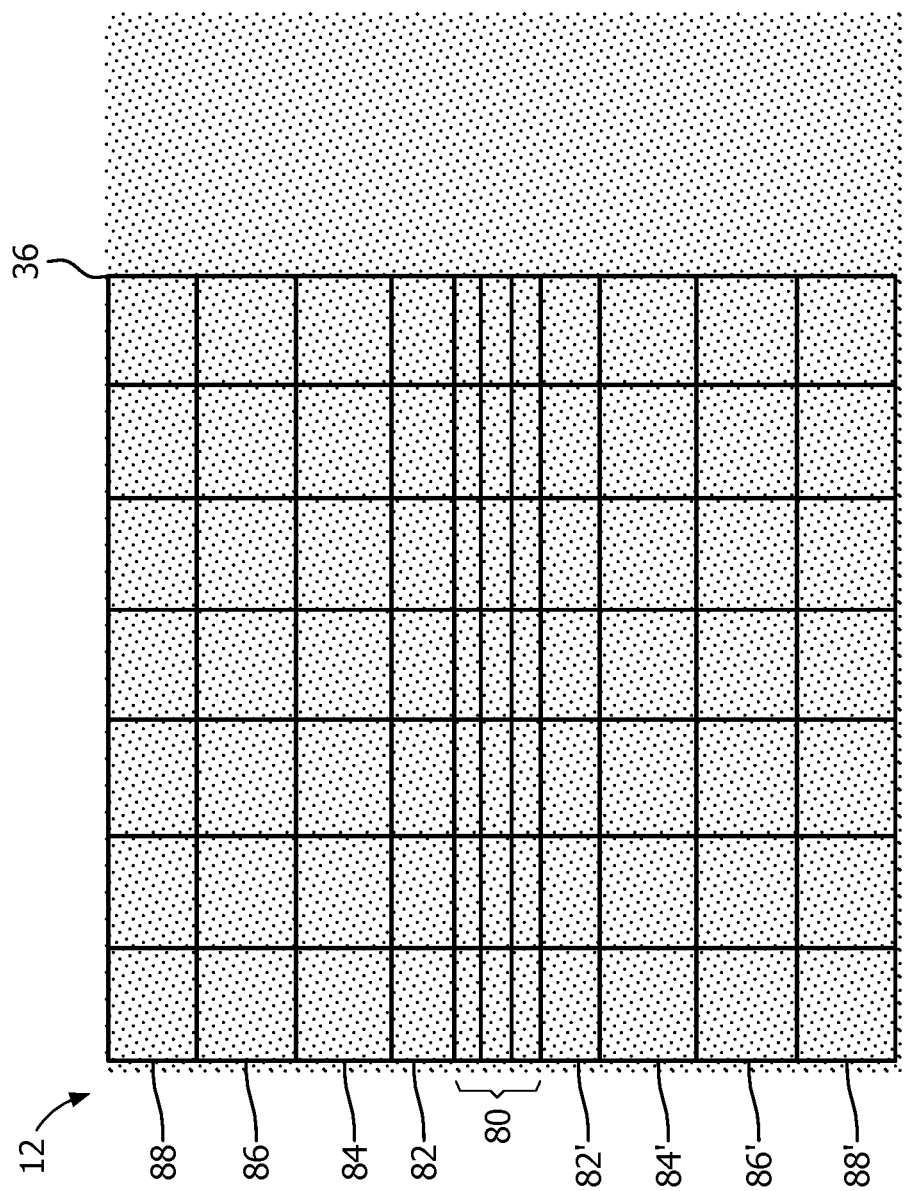
FIG. 5 illustrates the patch areas for elevation scanning with a 2D array transducer constructed in accordance with the principles of the present invention.
Figure 6:
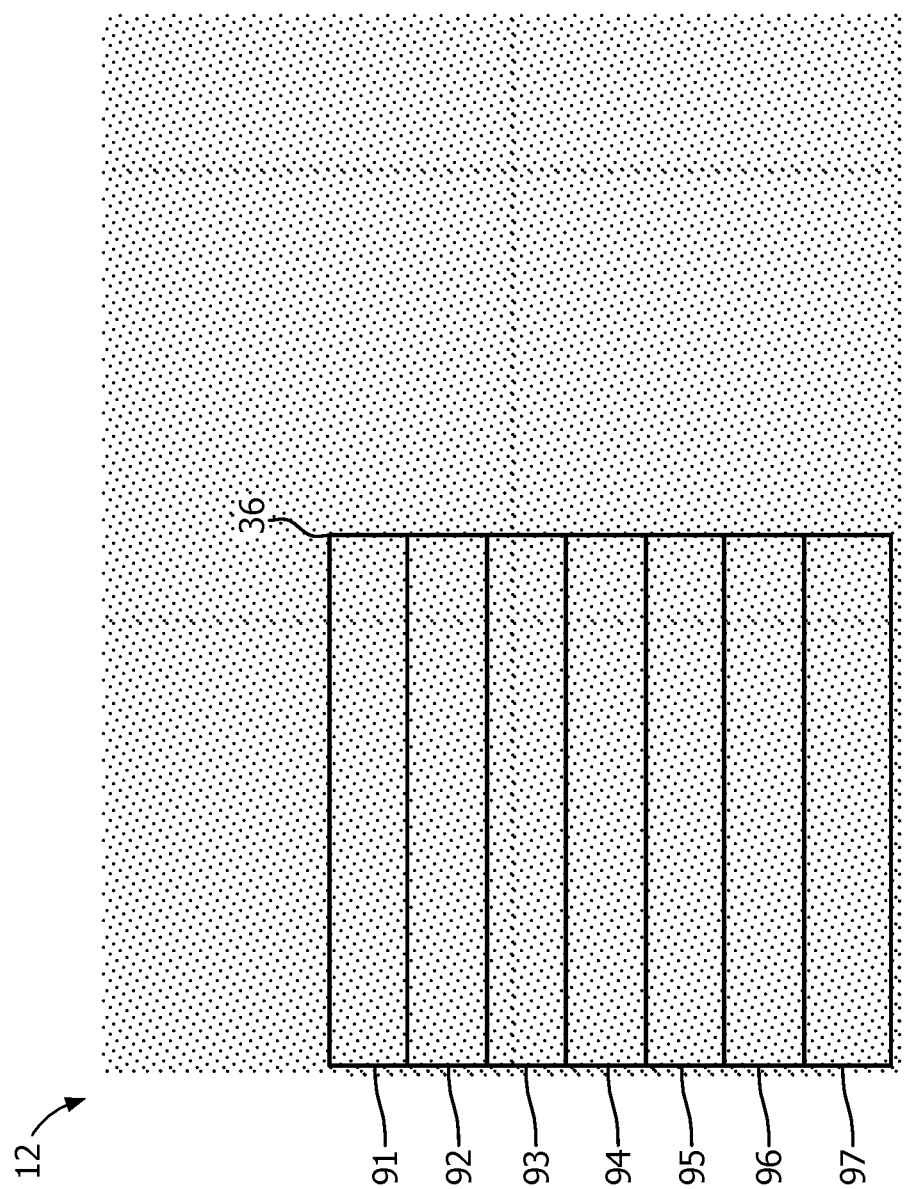
FIG. 6 illustrates the patch areas of a 2D array transducer for use with a low channel count system beamformer which does not need multiline acquisition.

While FIGS. 3b and 3c only illustrate one dimension of patches of an array transducer in accordance with the present invention, FIGS. 4-6 show topographic views of 2D arrays 12 which illustrate the dimensions of patches of exemplary 2D arrays of the present invention in both the azimuth (horizontal) and the elevation (vertical) dimensions. The 2D arrays 12 shown in these examples each comprise 160 elements in azimuth and 120 elements in elevation, a total of 19,200 elements in each 2D array. Four microbeamformer ASICs are used to do initial partial beamforming for each array. One ASIC is located behind each quadrant of an array as indicated by the faint lines 1-1 and 2-2 which delineate the ASIC boundaries. In FIGS. 4 and 5 the patches are outlined by the darker lines. In the Example of FIG. 4 there are seven rows of patches and sixteen columns of patches. This full aperture area 36 is seen to occupy less than the full area of the 2D array 12 so that the aperture can be translated in incremental steps across the 2D array for other spatially different scanlines as described in my U.S. Pat. No. 8,161, 817 (Savord). The aperture 36 of patches in FIG. 4 is seen to be at the left side of the 2D array and is then translated in steps to the right side.

The patches in the aperture 36 of FIG. 4 are smallest in the center of the aperture and largest at the azimuth edges of the aperture. Each row of patches in this example is 22 elements high in the elevation dimension; each patch is thus 22 elements in elevation. In the azimuth dimension the center four patches are three elements in width as indicated by the bracket 70 across the four center columns of patches. The next outermost columns of patches 72 and 72' are 4 elements wide and the next columns 74 and 74' are 5 elements wide. Patch columns 76 and 76' are 7 elements in elevation and patch columns 78 and 78' are 10 elements in elevation. The next outer columns 80 and 80' are 12 elements in elevation and the outermost columns 82 and 82' at the elevational limits of the aperture 36 are 14 elements wide. Reception with the 2D array of FIG. 4 would start by using the two or four small center patches initially at the shallowest depth, then progressively switching in the next adjacent patches on either side as echoes are received from greater depths until the full aperture of patches is active and used until the greatest desired depth of reception. This choice of patch arrangement is well suited for scanning a series of parallel or slightly tilted planes each extending in the azimuth direction across the volume being imaged.

If planes are to be scanned in the orthogonal direction, a set of planes which each extend in the elevation direction, a patch arrangement such as shown in FIG. 5 can be used. The active aperture 36 of the 2D array 12 of FIG. 5 has seven columns of patches extending in the elevation dimension which are uniformly sized in the azimuth (horizontal in the drawing) direction. In the elevation dimension the patch sizing varies from the smallest in the center of the aperture, the three rows of patches bracketed at 80 which are each six elements high in the elevation direction. The next outer patches indicated in rows 82 and 82' are each 12 elements high, and the next patches 84 and 84' are each 19 elements high. The two outermost rows at each elevation extreme, rows 86, 88, 86' and 88', are each 20 elements high. Scanning is performed by starting reception with the smallest patches 80 in the center, first one or all three, then progressively adding the adjacent patches in symmetrical pairs out from the center to grow the active aperture to the full aperture 36 at the greatest depth of field. As with the 2D array of FIG. 4, the active aperture 36 in FIG. 5 can be translated across the array in the azimuth direction to scan additional scanlines in the volumetric region in front of the array.

FIG. 6 illustrates an example of use of this 19,200 element 2D array 12 for imaging with an ultrasound system with only seven beamformer channels. As FIG. 6 shows, there are only seven patches 91-97 in the active aperture 36, the partially beamformed sum signals of each being coupled to a channel of the 7-channel beamformer of the ultrasound system. As before, the active aperture of seven patches can be translated to various other positions on the array. Each patch in this example comprises 1280 elements, 16 elements in the elevation direction and 80 elements in the azimuth direction. An aperture of this configuration would not generally be used for multiline scanning in azimuth, but could be used for low order multiline acquisition in elevation.

Figure 7:
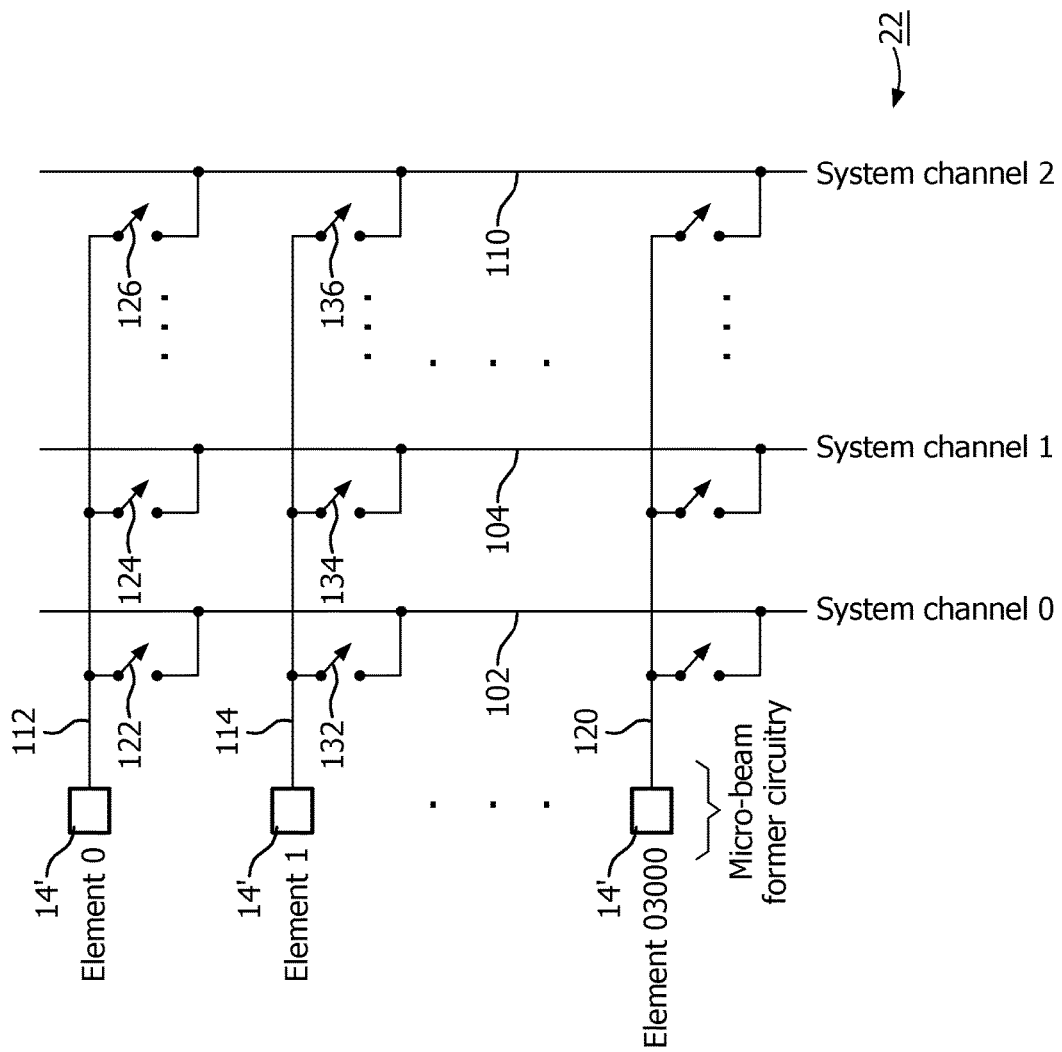
FIG. 7 illustrates a cross point switch matrix for coupling patches of a 2D array of various sizes to a system beamformer in accordance with the principles of the present invention.

FIG. 7 illustrates a cross point switching matrix suitable for selectively coupling microbeamformed signals from the probe microbeamformer 14 to channels of the system beamformer 22. Each element of the 2D array transducer, such as element 0, element 1, . . . element 3000 is coupled to circuitry 14' of the microbeamformer 14 which imparts an appropriate delay to the received signals. Each delayed element signal is conducted by a line 112, 114, . . . 120 to arms of electronic switches such as 122, 124, . . . 126 and 132, 134, . . . 136. One of the electronic switches on the line is closed to couple the signal from that element to a selected system beamformer channel such as system channel 0, system channel 1, . . . system channel 2. By selectively closing a desired switch in the cross point switching matrix, any delayed element signal can be put on a bus 102, 104, . . . 110 to sum with other signals on the bus and be applied to a channel of the system beamformer 22 for completion of the beamforming operation.

While the use of the present invention is particularly desirable when the probe uses a 2D array transducer, it is also advantageous for probes using 1D arrays which operate with a microbeamformer in the probe. Such an arrangement can be operated with ultrasound system beamformers of very low channel count such as system beamformers of only eight, ten, or twelve channels as described in U.S. patent application Ser. No. 61/503,329 (Poland et al.), filed Jun. 30, 2011. An implementation of the present invention can improve the multiline performance of 1D array/microbeamformer probes in systems with reduced channel count such as these.

What is claimed is:

1. A system for controlling an aperture of an array transducer, the system comprising:
   an ultrasound probe comprising a microbeamformer that is configured to perform at least partial beamforming of received echo signals; and
   a processor configured to perform the following steps:
   form the aperture of the array into a plurality of patches of different sizes, each patch of the plurality of patches comprising a group of transducer elements coupled to the microbeamformer;
   receive echo data from a shallow depth of field with an active aperture comprising one or more patches of the plurality of patches, wherein each of the one or more patches have a first size; and
   receive echo data from a deeper depth of field by growing the active aperture to add patches each having a second size larger than the first size;
   wherein the processor is further configured to form patches of a uniform size in a first dimension and a different size in a second dimension, such that a smallest patch is positioned in a center of the aperture in either the first dimension or the second dimension with patches of progressively increasing size positioned on either side of the smallest patch in either the first dimension or the second dimension.

2. The system of claim 1, wherein the array transducer comprises a two dimensional (2D) array of transducer elements.

3. The system of claim 1, wherein receiving the echo data from a deeper depth of field further comprises growing the active aperture symmetrically about the one or more patches of the first size.

4. The system of claim 1, wherein receiving the echo data from a deeper depth of field further comprises growing the active aperture asymmetrically about the one or more patches of the first size.

5. The system of claim 1, wherein receiving echo data from a deeper depth of field further comprises growing the active aperture to add patches of a largest size on either side of the patches of a larger size.

6. The system of claim 2, wherein the processor is further configured to translate the active aperture to different groups of transducer elements of the 2D array.

7. The system of claim 1, wherein the first dimension comprises a vertical dimension.

8. The system of claim 7, wherein the second dimension comprises a horizontal dimension.

9. The system of claim 8, wherein the processor is further configured to form the smallest patch in the center of the aperture in the horizontal dimension with patches of progressively increasing size extending on either side of the smallest patch to the horizontal limits of the aperture on either side of the smallest patch.

10. The system of claim 1, wherein the first dimension comprises a horizontal dimension and the second dimension comprises a vertical dimension.

11. The system of claim 10, wherein the processor is further configured to form the smallest patch in the center of the aperture in the vertical dimension with patches of progressively increasing size extending on either side of the smallest patch to the vertical limits of the aperture on either side of the smallest patch.

12. The system of claim 1, further comprising an ultrasound system beamformer configured to complete beamforming of the partially beamformed signals.

13. The system of claim 12, wherein signals from the elements of a patch are coupled to a channel of an ultrasound system beamformer with a cross point switch.

14. The system of claim 13, wherein the microbeamformer is configured to generate a patch sum signal and the elements of a patch are coupled to a common bus.

15. The system of claim 14, wherein the microbeamformer is configured to delay the signals from the elements to form the patch sum signal.

* * * * *